United States Patent
Nycz et al.

(10) Patent No.: US 7,362,228 B2
(45) Date of Patent: Apr. 22, 2008

(54) SMART INSTRUMENT TRAY RFID READER

(75) Inventors: Jeffrey H. Nycz, Collierville, TN (US); Steven M. Tethrake, North Webster, IN (US)

(73) Assignee: Warsaw Orthepedic, Inc.

( * ) Notice: Subject to any disclaimer, the term of this patent is extended or adjusted under 35 U.S.C. 154(b) by 248 days.

(21) Appl. No.: 11/116,360

(22) Filed: Apr. 28, 2005

(65) Prior Publication Data

US 2006/0244593 A1    Nov. 2, 2006

(51) Int. Cl.
*G08B 13/14* (2006.01)
(52) U.S. Cl. ............... 340/572.1; 340/568.1; 340/539.1; 206/363; 206/370; 211/88.01
(58) Field of Classification Search ............ 340/572.1, 340/568.1, 572.8, 539.1, 539.12, 539.11, 340/517, 521; 206/363, 370, 364, 365; 211/88.01, 211/85.13; 128/852, 846

See application file for complete search history.

(56) References Cited

U.S. PATENT DOCUMENTS

| | | | |
|---|---|---|---|
| 4,075,632 | A | 2/1978 | Baldwin et al. |
| 4,360,801 | A | 11/1982 | Duhame |
| 4,390,880 | A | 6/1983 | Henoch |
| 4,688,026 | A * | 8/1987 | Scribner et al. ............ 235/385 |
| 4,739,328 | A | 4/1988 | Koelle et al. |
| 5,030,807 | A | 7/1991 | Landt et al. |
| 5,381,896 | A * | 1/1995 | Simons ....................... 206/370 |
| 5,540,901 | A * | 7/1996 | Riley .......................... 422/300 |
| 5,621,199 | A | 4/1997 | Calari et al. |
| 5,923,001 | A | 7/1999 | Morris et al. |
| 5,963,134 | A * | 10/1999 | Bowers et al. ........... 340/572.1 |

(Continued)

FOREIGN PATENT DOCUMENTS

EP    1 442 715 A2    8/2004

OTHER PUBLICATIONS

Presentation by Innovision Research and Technology, PLC at the "RFID in Healthcare" conference in Washington, DC. on Dec. 2 and 3, 2003.

(Continued)

*Primary Examiner*—Benjamin C. Lee
*Assistant Examiner*—Daniel Previl
(74) *Attorney, Agent, or Firm*—Goodwin Procter LLP (57) ABSTRACT

A radio frequency identification (RFID) workstation reader for RFID-enabled surgical instruments and surgical instrument trays and a method of using a RFID workstation reader to read RFID-enabled surgical instruments and surgical instrument trays is disclosed. The method, apparatus, and system enable individual instruments or a surgical instrument tray containing several surgical instruments to be quickly and efficiently inventoried and tracked. An instrument or instrument tray is placed on the workstation reader. An RF field generated by a plurality of antennae, causes RFID tags embedded in or attached to the instrument or instrument tray to emit a signal containing item specific identification information stored in the tags. The information is received by a control circuit and passed to a computer for data analysis. A status LED is illuminated on the workstation reader based on the results of the data analysis. The method, apparatus, and system can track, inspect, and verify inbound and outbound surgical instrument kits, and help to assess the surgical instruments' and trays' duty life cycle usage.

17 Claims, 4 Drawing Sheets

U.S. PATENT DOCUMENTS

| | | | |
|---|---|---|---|
| 6,158,437 A | 12/2000 | Vagley | |
| 6,164,738 A | 12/2000 | Dane et al. | |
| 6,318,636 B1 | 11/2001 | Reynolds et al. | |
| 6,366,206 B1* | 4/2002 | Ishikawa et al. | 340/573.1 |
| 6,405,863 B1 | 6/2002 | Dhindsa | |
| 6,415,978 B1 | 7/2002 | McAllister | |
| 6,426,041 B1* | 7/2002 | Smith | 422/28 |
| 6,429,776 B1 | 8/2002 | Alicot et al. | |
| 6,480,101 B1 | 11/2002 | Kelly et al. | |
| 6,523,752 B2 | 2/2003 | Nishitani et al. | |
| 6,646,241 B1 | 11/2003 | Varma et al. | |
| 6,669,089 B2 | 12/2003 | Cybulski et al. | |
| 6,692,495 B1 | 2/2004 | Zacouto | |
| 6,752,277 B1* | 6/2004 | Sempliner | 211/59.3 |
| 6,777,623 B2 | 8/2004 | Ballard | |
| 6,825,766 B2 | 11/2004 | Hewitt et al. | |
| 6,853,303 B2* | 2/2005 | Chen et al. | 340/573.1 |
| 6,861,954 B2 | 3/2005 | Levin | |
| 6,866,147 B2 | 3/2005 | Barwick | |
| 7,019,650 B2* | 3/2006 | Volpi et al. | 340/572.1 |
| 7,080,755 B2* | 7/2006 | Handfield et al. | 221/13 |
| 2002/0032435 A1 | 3/2002 | Levin | |
| 2002/0063622 A1 | 5/2002 | Armstrong et al. | |
| 2002/0067263 A1* | 6/2002 | Tafoya et al. | 340/572.1 |
| 2002/0105424 A1 | 8/2002 | Alicot et al. | |
| 2002/0143320 A1 | 10/2002 | Levin | |
| 2002/0188259 A1 | 12/2002 | Hickle et al. | |
| 2003/0164401 A1 | 9/2003 | Andreasson et al. | |
| 2003/0174099 A1 | 9/2003 | Bauer et al. | |
| 2003/0189094 A1 | 10/2003 | Trabitz | |
| 2003/0196837 A1 | 10/2003 | Ballard | |
| 2004/0008123 A1 | 1/2004 | Carrender et al. | |
| 2004/0022227 A1 | 2/2004 | Lynch et al. | |
| 2004/0031626 A1 | 2/2004 | Morris et al. | |
| 2004/0069851 A1 | 4/2004 | Grunes et al. | |
| 2004/0100384 A1 | 5/2004 | Chen et al. | |
| 2004/0160233 A1 | 8/2004 | Forster | |
| 2004/0174244 A1 | 9/2004 | Eidemiller | |
| 2004/0174261 A1 | 9/2004 | Volpi et al. | |
| 2004/0186576 A1 | 9/2004 | Biscup et al. | |
| 2004/0220602 A1 | 11/2004 | Deng et al. | |
| 2004/0220860 A1 | 11/2004 | Persky et al. | |
| 2004/0250819 A1 | 12/2004 | Blair et al. | |
| 2004/0267297 A1 | 12/2004 | Malackowski | |
| 2005/0003757 A1 | 1/2005 | Anderson | |
| 2005/0012617 A1 | 1/2005 | DiSilvestro et al. | |

OTHER PUBLICATIONS (http://rfidjournal.com/article/view/112) RFID Journal, Can RFID Cure Healthcare's Ills?, Nov. 12, 2002.

(http://www.eetimes.com/showPressRelease.jhtml?articleID=57907) EE Times (www.eetimes.com) "T-Ink™ Unique Conductive Ink Technology to Be Featured" Feb. 14, 2003, pp. 1-2.

(http://americanprinter.com/microsites/magazinearticle.asp?mode=print&magazinearticleid...) American Printer (www.americanprinter.com) "Tracking RFID Progress" Jan. 1, 2004, pp. 1-3.

* cited by examiner

SMART INSTRUMENT TRAY RFID READER

FIELD OF THE INVENTION

The invention generally relates to a surgical instrument tray apparatus and method for implementing radio frequency identification techniques to inventory the contents of a surgical instrument tray, and more particularly to a surgical instrument tray apparatus and method for wirelessly inventorying surgical instruments located on or in the surgical instrument tray to facilitate tracking and inventory management of surgical instruments over their useful life cycle.

BACKGROUND OF THE INVENTION AND DESCRIPTION OF RELATED ART

Surgical instrument storage and sterilization systems are known in the art. These systems, referred to as surgical instrument trays or surgical instrument kits, typically consist of metal or plastic trays that hold a variety of general purpose and/or procedure specific surgical instruments such as forceps, scissors, clamps, retractors, scalpels, etc. These surgical instrument trays are brought into the operating room (OR) when preparing for surgery, and also are used as a means to organize, transport and store surgical instruments in a medical facility.

Due to advances in medical technology that have increased the number of surgical instruments now in use and due to the constant pressure in the health care industry to reduce operating costs, it has become necessary to manage and track these instruments more quickly and efficiently. One advancement towards this end has been the creation of surgical instrument trays that employ various techniques for controlling the arrangement of instruments on the tray so that any missing instruments can be identified quickly. Once such method is disclosed in U.S. Pat. No. 6,158,437, which uses a combination of instrument identifying indicia including a plurality of graphical indicia that represent an outline of the basic shape of each instrument, as well as a terse written description of the instrument to identify the correct placement of specific surgical instruments on the tray. Another such method is disclosed in U.S. Pat. No. 6,426,041, which utilizes a plurality of recessed sections of applicable shape and size distributed on the work surface of the tray to accommodate specific instruments. Upon extraction from the tray, the instruments are in ready position to be relayed to the person performing the operation. U.S. Pat. Nos. 6,158,437 and 6,426,041 are hereby incorporated by reference in their entireties. Through implementation of the teachings of these patents, a person can visually inspect a surgical instrument tray and make a determination as to whether any instruments are missing or misplaced.

Another function provided by surgical trays is to facilitate group sterilization. Sterilization is of paramount importance in a surgical setting such as a hospital to prevent potentially deadly infections to patients undergoing surgery. Prior to every surgical procedure, all surgical instruments and trays must be sterilized. Also, following each surgical procedure, all instruments on a given tray, if not wrapped separately, whether soiled or not, must be re-sterilized before subsequent usage. In order to increase the speed and efficiency of sterilization, entire surgical trays containing several instruments often are placed in a sterilization chamber at once. The sterilization chamber may provide any combination of heat, pressure, and/or fluid or vaporous sterilant to the trays and all the instruments contained therein. Sterilization techniques are ubiquitously well known in the art. Thus, a detailed discussion of them has been intentionally omitted.

Over time, and through ordinary usage, as well as due to the sterilization process, surgical instruments suffer wear and tear and eventually reach the end of their life cycle. Thus, it has become necessary to periodically inspect and maintain records on usage of surgical instruments so that they can be replaced as necessary. Also, due to the fact that they are constantly moved from the operating room to sterilization, to storage, and back to the operating room, various instruments on a given tray may become lost, or unrelated instruments from other trays may be added. Because certain instruments are so specialized that there are no functional substitutes, it has become necessary to regularly inspect trays for any missing instruments and to readily identify specific instruments that are missing. Existing methods for performing these necessary functions are overly reliant on costly human interpretation. Also, in some cases, a skilled technician may be required to identify missing instruments. As with any human inspection process, the results are limited by the skill and accuracy of the person doing the inspecting.

Several methods currently exist for tracking and providing information about inventoried items that may be useful for tracking surgical instruments and trays. For example, in retail and manufacturing applications, inventory items typically carry printed labels providing information such as serial numbers, price, weight, manufacturing or use dates, and size. Usually, these labels are not machine readable, but rather require human interpretation. Another method for tracking and providing information about items that ameliorates some of the short comings of printed labels is bar code labeling. Bar code labels are characterized by a pattern of vertically oriented machine readable variable width bars that, when illuminated with a bar code scanner, create a reflection pattern that translates into a unique series of numbers. The series of numbers must then be correlated to product descriptions in a relational database in communication with the bar code scanner for purposes of identification, price checking, and inventory management.

Bar code labels have received widespread use from product tracking in the package delivery business, to physical inventory tracking and even point-of-sale terminals. In some respects, due to their machine readable nature, bar code labels represent a significant improvement over printed labels. Also, they are relatively cheap and easy to generate with a printer. There are some restrictions to bar codes, however, that limit their application to surgical instruments and trays. Bar codes are limited in size by resolution limitations of bar code scanners, and the amount of information that the symbols can contain is limited by the physical space constraints of the label. Therefore, some objects may be unable to accommodate bar code labels because of their size and physical configuration. In the field of surgical instruments, this may preclude bar code labels from some smaller or non-geometrically shaped instruments. In addition, labels only store a number that is meaningless until associated with a database.

Another limitation of bar code readers is that they require line of sight in order to read the reflection pattern from a bar code. As labels become worn or damaged, and they can no longer be read with the bar code scanner. This is particularly likely in the field of surgical instrument trays because of the harsh conditions the labels must undergo during sterilization. Also, because a person operating the bar code scanner must physically orient either the scanner or the product to achieve line of sight on each item being scanned, items must be scanned one at a time resulting in prolonged scan time. In addition, because bar code scanning requires the operator to handle each instrument in order to scan it, a potential safety problem is created. Soiled instruments pose a biohazard because they may have come in contact with bodily fluids, and often have sharp edges. After the instruments have been sterilized, they should not be touched again until surgery to prevent contamination. Therefore, direct human contact either pre or post sterilization may be problematic. Another limitation of bar code labels is that they are static. Updating the information in these machine-readable symbols requires printing a new label to replace the old.

Data carriers such as memory devices provide an alternative method for tracking and providing information about items. Memory devices permit linking of large amounts of data with an object or item. Memory devices typically include a memory and logic in the form of an integrated circuit ("IC") and a mechanism for transmitting data to and/or from the product or item attached to the memory device. A promising memory device-based product identification technology that ameliorates many of the above noted deficiencies of both printed labels and bar coded labels is that of radio frequency identification (RFID). RFID systems use an RF field generator and a plurality of RFID tags attached to goods and products to store and retrieve information about the goods and products. RFID tags are miniature electronic circuits that store identification information, usually in the form of a number, about the products they are attached to. An RFID transponder tag typically includes a memory for storing data, an antenna, an RF transmitter, and/or an RF receiver to transmit data, and logic for controlling the various components of the memory device. The basic structure and operation of RFID tags can be found in, for example, U.S. Pat. Nos. 4,075,632, 4,360,801, 4,390,880, 4,739,328 and 5,030,807, the disclosures of which are hereby incorporated by reference in their entirety.

RFID tags generally are formed on a substrate and can include, for example, analog RF circuits and digital logic and memory circuits. RFID tags also can include a number of discrete components, such as capacitors, transistors, and diodes. The RF transmission of data can be accomplished with modulated back scatter as well as modulation of an active RF transmitter. RFID tags typically come in one of two types: active or passive. Active tags are characterized in that they have their own power source, such as a battery. When they enter an RF field they are turned on and then emit a signal containing their stored information. Passive tags do not contain a discrete power source. Rather, they become inductively charged when they enter an RF field. Once the RF field has activated the passive circuit, the tags emit a signal containing their stored information. Passive RFID tags usually include an analog circuit that detects and decodes the interrogating RF signal and that provides power from the RF field to a digital circuit in the tag. The digital circuit generally executes all of the data functions of the RFFD tag, such as retrieving stored data from memory and causing the analog circuit to modulate to the RF signal to transmit the retrieved data. In addition to retrieving and transmitting data previously stored in the memory, both passive and active dynamic RFID tags can permit new or additional information to be stored in the RFID tag's memory, or can permit the RFID tag to manipulate data or perform some additional functions.

An advantage of RFID tags over other machine readable ID tags such as bar code tags is that they do not require line of sight to be read by an RFID reader. Because RF waves can penetrate surfaces impervious to light waves, the tags can be encapsulated into ruggedized containers. Furthermore, a group of tags placed within the influence of an RFID reader can read in batch mode. Also, in the cases of dynamic RFID tags, information stored in the tags can be updated allowing them to serve as transactional records.

Due in part to a relative increase in cost over equivalent bar code-based systems, RFID tags were originally used only on items of sufficiently high value to justify their use or in environments where bar coding was not possible such as anti theft protection. However, with the price of RFID tags now reaching as low as 5 cents per tag, and because of reductions in size due to an overall trend towards miniaturization in circuit design, RFID tags are currently being applied to many types of products, both at the consumer level as well as in manufacturing processes. RFID tags provide a robust yet cost effective solution to inventory tracking and management.

The description herein of various advantages and disadvantages associated with known apparatus, methods, and materials is not intended to limit the scope of the invention to their exclusion. Indeed, various embodiments of the invention may include one or more of the known apparatus, methods, and materials without suffering from their disadvantages.

SUMMARY OF THE INVENTION

Thus, there exists a need to provide an inventory management system for surgical instruments and surgical trays that reduces handling costs and provides accurate and rapid tracking of instruments over their lifecycle.

Embodiments of the present invention mitigate or solve the above-identified limitations in known solutions, as well as other unspecified deficiencies in known solutions. A number of advantages associated with various embodiments of the present invention are readily evident to those skilled in the art, including economy of design and resources, transparent operation, cost savings, etc. Various exemplary embodiments according to the method and apparatus of the present invention allow for lower handling costs of surgical instruments, increase the accuracy of the verification process of data pertaining to each instrument with a reduction of human contact, and provide real-time data collection resulting in fast data acquisition, which ultimately speeds up inventory updating of such instruments.

In accordance with one embodiment of the present invention, an surgical instrument tray apparatus is provided that is capable of wirelessly inventorying surgical instruments contained in or on the tray by retrieving information from the instrument through RFID technology. An RFID system in accordance with embodiments of this invention preferably includes at least three components: (i) an antenna; (ii) a transceiver (often the antenna and transceiver are combined into one reader); and (iii) a transponder (the RF tag) electronically programmed with certain unique information. The antenna emits radio frequency waves to activate the transponder (tag) in order to read or write data to it. In turn, the tag transmits data back to the antenna, and the data can be used to interface with a database to carry out a function such as inventory processing. The apparatus comprises a surgical instrument tray having an integral RFID transceiver and control circuit, one or more RF antennae, a power supply and visual indicator. Surgical instruments located on or in the surgical instrument tray possess RFID tags either attached or integral thereto that store identification information about their respective instruments. Upon activation, the RF antennae generate an RF field which activates the RFID tags of the surgical instruments causing them each to emit signals containing information stored in the tags. This information, usually an identification number associated with that instrument, is compared against the contents of a memory integral to the instrument tray circuitry that has been pre-programmed with the identification numbers of instruments that are supposed to be associated with that instrument tray. If all instruments are present, a green LED integral to a side surface of the surgical instrument tray is illuminated. Otherwise, a red LED is illuminated.

In one embodiment of the invention, an apparatus for identifying surgical instruments is disclosed. The apparatus of this embodiment comprises a surgical instrument tray for accommodating one or more surgical instruments. Located within the body of the surgical instrument tray is an RF transceiver unit, including a controller and one or more RF antenna transceivers, for projecting an RF field onto at least one surface of the surgical instrument tray to activate an RFID transponder tag associated with a surgical instrument and to receive a signal emitted by the RFID transponder tag. On a surface of the surgical instrument tray is an activation switch located for activating the tray to perform a data processing function. A data processor is electrically coupled to the RF transceiver unit, and is operable to compare the signal emitted by the RFID transponder tag with a value stored in memory. Finally, a visual indicator located at least one surface of the surgical instrument tray is operable to give a visual indication of a current state of the surgical instrument tray based on the comparison. A power supply in the form of a battery provides electricity to the various enumerated electrical components.

In another embodiment of this invention, an electrical circuit used in an RF reader enabled surgical instrument tray is disclosed. In this embodiment, the electrical circuit comprises a controller including a processor and a memory, an RF transceiver including one or more RF antennae, a power supply, an activation switch, and a visual indicator.

In yet another embodiment of this invention, a method of performing an inventory function with an RF enabled surgical instrument tray is disclosed. The method according to this embodiment comprises activating the RF enabled surgical instrument tray, projecting an RF field at one or more surgical instruments of said instrument tray to active an RFID tag associated with each of the one or more surgical instruments, receiving a signal containing identification information from each RFID tag, comparing said identification information against previously stored data, and providing a visual indication of the results of said comparison.

In an additional embodiment according to this invention, a computer readable storage medium storing instructions therein for causing a computer processor to perform functions related to inventorying surgical instruments for use in an RFID reader enabled surgical instrument tray is disclosed. The storage medium according to this embodiment comprises instructions for generating an RF field with one or more RF antenna transceivers to activate an RF transponder tag associated with each of one or more surgical instruments. The storage medium also comprises instructions for receiving a signal emitted by each of the RF transponder tags containing identification information relating to items that the tags correspond to and instructions for comparing said identification information to information stored in a memory of said surgical instrument tray to determine if said identification information matches said stored information. Finally, the storage medium according to this embodiment comprises instructions for generating a visual indication of whether said identification information matches said stored information.

Other aspects and advantages of the invention will become apparent from the following detailed description, taken in conjunction with the accompanying drawings, illustrating by way of example the principles of the invention.

BRIEF DESCRIPTION OF THE DRAWINGS

Purposes and advantages of the present invention will be apparent to those of ordinary skill in the art from the following detailed description in conjunction with the appended drawings in which like reference characters are used to indicate like elements, and in which.

DETAILED DESCRIPTION OF THE DISCLOSURE

The following description is intended to convey a thorough understanding of the invention by providing specific embodiments and details involving automating and adding value to medical and surgical instruments, and instrument kits. It is understood, however, that the invention is not limited to these specific embodiments and details, which are exemplary only. It further is understood that one possessing ordinary skill in the art, in light of known systems and methods, would appreciate the use of the invention for its intended purposes and benefits in any number of alternative embodiments, depending upon specific design and other needs.

Figure 1:
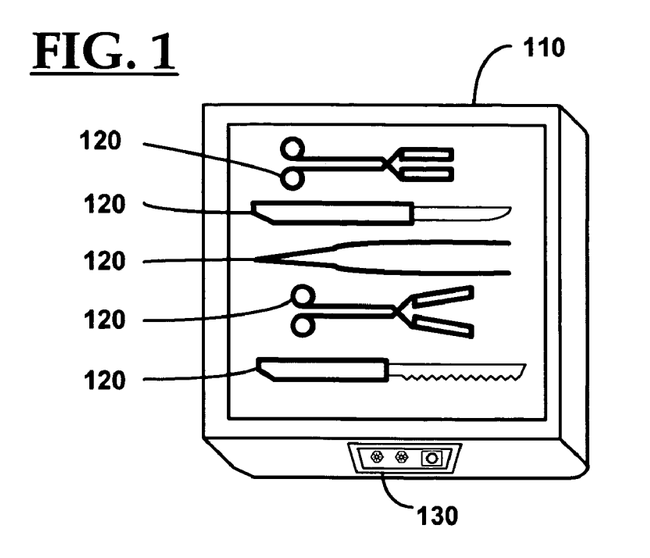
FIG. 1 is a schematic diagram of an RFID enabled smart surgical instrument tray containing a plurality of RF transponder tag enabled surgical instruments and a status indicating LED in accordance with an embodiment of the invention.

Referring to FIG. 1, a surgical instrument tray 110 and a plurality of surgical instruments 120 are illustrated in accordance with one exemplary embodiment of this invention. As shown in FIG. 1, the surgical instrument tray 110 comprises a box-like structure having a hollowed body and a roughly planar top surface surrounded on its perimeter by a raised lip that prevents instruments from sliding off of the tray. Typically, surgical instrument tray bodies are made of a plastic or other non-corrosive, relatively lightweight material such as titanium or stainless steel. In FIG. 1, for purposes of example only, the surgical instrument tray 110 is shown as being flat. However, it should be noted that surgical instrument trays may also contain one or more recesses shaped to receive various surgical instruments without departing from the spirit or scope of this invention. Alternatively, the surgical instrument tray may be of a kit configuration in which surgical instrument are placed inside the tray body in a drawer or box such that they can be enclosed by the tray body when direct access to the individual instruments is not required.

With continued reference to FIG. 1, the surgical instrument tray 110 also comprises a status indicating panel 130 including an activation switch for activating the tray to perform an inventory function. For purposes of example only, five surgical instruments 120 are shown residing of the top surface of the surgical instrument tray 110. Each surgical instrument 120 shown on the tray 110 comprises an RFID transponder tag storing identification information for that instrument. As will be discussed further in relation to the remaining figures, depressing the activation button will cause the tray 110 to wirelessly inventory its contents by reading the contents of each RFID transponder tag, and to give a visual indication of the results of the inventory on the status panel 130.

Figure 2:
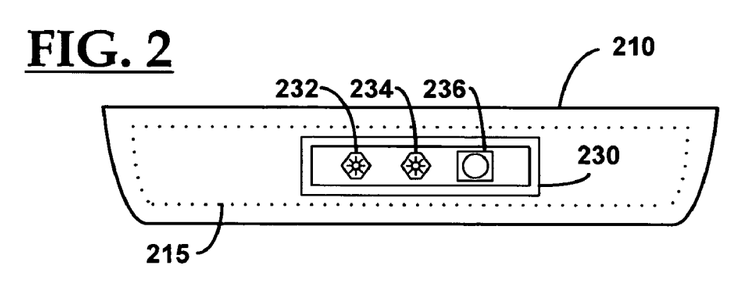
FIG. 2 is a profile view of the RFID enabled smart surgical instrument tray of FIG. 1 according to an embodiment of the invention.

Referring now to FIG. 2, a profile view of a surgical instrument tray 210 is shown in accordance with an embodiment of this invention. As discussed above in the context of FIG. 1, the surgical instrument tray 210 shown in FIG. 2 includes a hollowed body having an inner peripheral wall 215 and also status indicating LED panel 230. In various exemplary embodiments, the status indicating LED panel includes a green LED 232, a red LED 234 and an activation button/switch 236. Upon depressing of the activation button/switch 236, the smart RFID surgical instrument tray 210 reads the contents of any RFID transponder tags attached or integral to any surgical instruments on the tray 210. In various exemplary embodiments, a non-volatile memory located in an integral circuit in the tray stores a list of surgical instruments that should be included with that particular tray. Therefore, based on a comparison between the instruments that should be present and those that actually are present, one of either the green LED 232 or the red LED 234 are illuminated.

Figure 3:
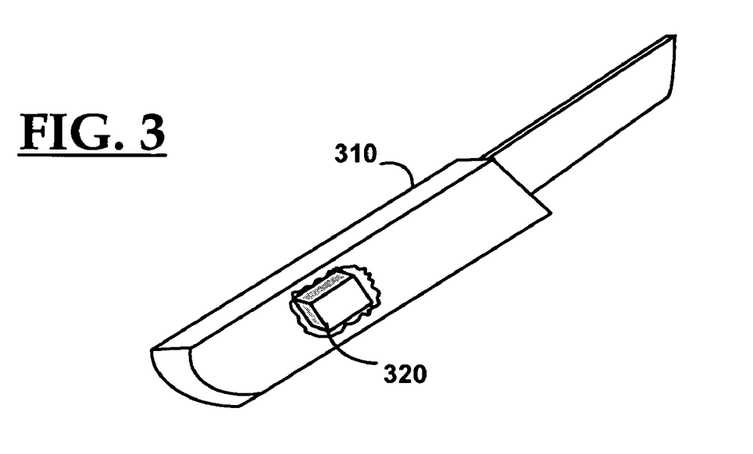
FIG. 3 is a cutaway diagram of an exemplary surgical instrument shown in FIG. 1 having an embedded RFID tag according to an embodiment of the invention.

FIG. 3 illustrates an exemplary surgical instrument 310 containing an embedded RFID transponder tag 320 in accordance with various exemplary embodiments of this invention. In FIG. 3, a scalpel 310 is shown having an RFID transponder tag 320 embedded in its handle. Although FIG. 3 illustrates the RFID tag 320 as being embedded in the handle by way of a cut-away opening, usually, in such an embodiment, the RFID tag 320 will be concealed within the handle of the instrument 310. Because RF waves can penetrate surfaces impenetrable to light waves, it is not necessary for the RFID transponder tag 320 to be located on an exterior surface of the surgical instrument 310. However, it should be appreciated that the RFID transponder tag 320 is shown as being embedded merely for illustrative purposes only. Obviously, in order for the RFID transponder tag 320 to be embedded in the surgical instrument 310, it would have to have been manufactured that way. Thus, in order not to preclude application of the invention to existing surgical instruments, it should be appreciated that the RFID transponder tag 320 may be affixed to an external surface of a surgical instrument or may even be attached to the surgical instrument 320 using any suitable attachment means. Such attachment means may include, but should not be limited to an adhesive, a cable or wire, or other attachment means. Furthermore, different surgical instruments having different shapes and dimensions may require different attaching means. The particular mechanism selected to attach RFID transponder tags to the surgical instruments is not critical to this invention.

Still referring to FIG. 2, the RFID tag 320 preferably includes a combined receiving and transmitting antenna, and a transceiver, which can contain one or more amplifiers, key means, saw tooth pulse generator, a frequency converter, and electronically programmable, integrated circuit memory. The integrated circuit memory may be a random access memory (RAM). The tag 320 preferably is adapted to deliver stored information to the RFID workstation reader upon instruction or request therefrom. The storing of information in the memory of the RFID tag can be accomplished in accordance with the procedures set forth in U.S. Pat. No. 4,390,880, the disclosure of which is incorporated by reference herein in its entirety.

In various exemplary embodiments, the RFID transponder tag 320 will contain information specific to the instrument that it is attached or integral to. For example, the RFID transponder tag 320 may contain information including but not limited to the manufacturer of the instrument, the manufacturing date, a serial or id number for the instrument, a name for the instrument (i.e., scalpel, forceps, etc.). In this manner, the identification information stored in the RFID transponder tag for each instrument can be compared against list of identification information stored in the smart surgical tray RFID reader corresponding to items that should be on the tray. Alternatively, the RFID transponder tags may merely contain a serial number and/or other field which can than be used to query a relational database stored in a memory of the smart instrument tray RFID reader in which the list of instruments belonging to that tray are stored in association with their serial number and/or name.

Figure 4:
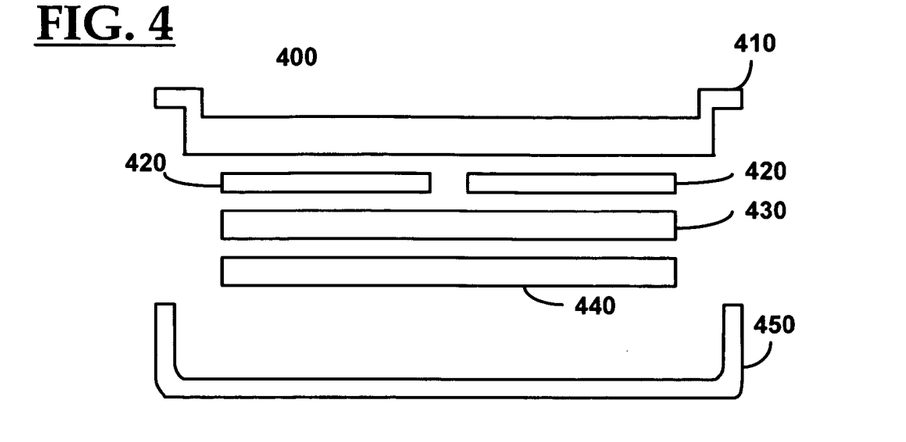
FIG. 4 is a cross-sectional exploded cut away view of an RFID enabled smart surgical instrument tray according to one embodiment of this invention.

FIG. 4 is a cross-sectional exploded cut away view of an RFID enabled smart surgical instrument tray 400 according to one embodiment of this invention. In FIG. 4, the smart instrument tray 400 is shown comprising a tray body consisting of a lower body portion 450 and a tray top portion 410, two RF antennae 420, an RF transceiver control circuit 430 and a power supply 440, such as a battery. In various exemplary embodiments, the battery 440 may be a permanent battery designed to last the entire useful life of the surgical instrument tray 400. In various other embodiments, the battery 440 may be a disposable battery which can be replaced when it has been drained of its stored power. In yet other embodiments, the battery 400 may be a rechargeable battery that is recharged through a power interface connector (not shown) disposed on at least one surface of the surgical instrument tray 400. The invention is fully compatible with any of the above battery configurations.

Figure 5:
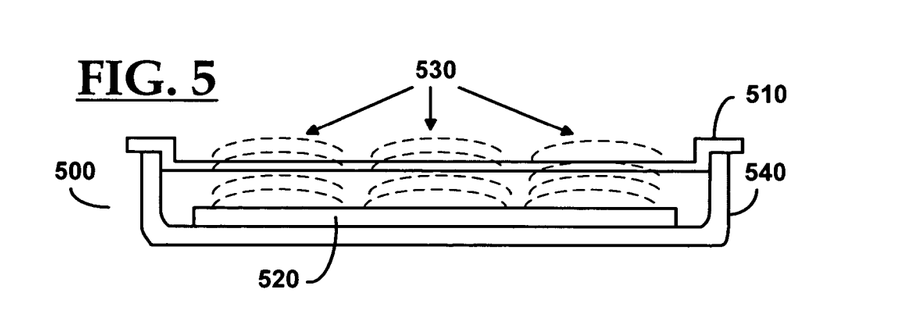
FIG. 5 is a cross-sectional cut away view of a surface-type RFID enabled smart surgical instrument tray according to one embodiment of this invention.

FIG. 5 is a cross-sectional cut away view of a surface-type RFID enabled smart surgical instrument tray 500 according to one embodiment of this invention. As shown in FIG. 5, the internal components of the smart instrument tray 500, for example, those shown in FIG. 4, are located inside the tray housing and are showed as being lumped together in a single enclosure 520. In the surface-type tray 500, surgical instruments are placed on the top surface of the tray 510. In such a configuration, RF inventorying is performed by projecting an RF field 530 upward through the tray's top surface 510. This RF field 530 will energize the RFID transponder tags of any instruments located on the tray surface and the RF transceiver unit in the enclosure 520 will then read the signals emitted by the energized tags.

Figure 6:
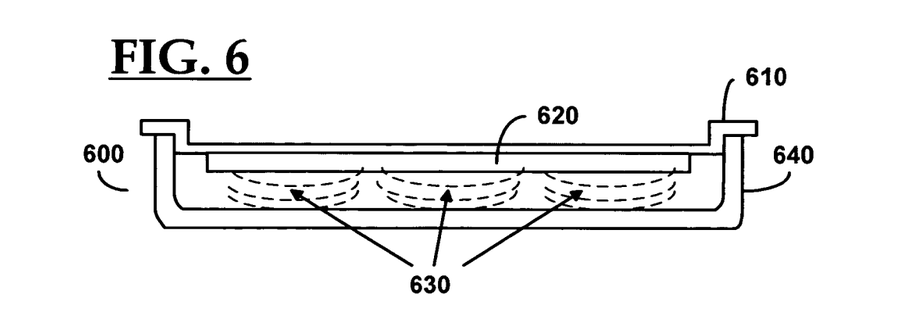
FIG. 6 is a cross-sectional cut away view of a kit-type RFID enabled smart surgical instrument tray according to one embodiment of this invention.

FIG. 6 is a cross-sectional cut away view of a kit-type RFID enabled smart surgical instrument tray 600 according to one embodiment of this invention. As shown in FIG. 6, and in a manner analogous to that of FIG. 5, the internal components of the smart instrument tray 600, are contained in the tray body in a single enclosure 620. However, in the embodiment illustrated in FIG. 6, the internal components in the enclosure 620 are mounted to the underside of the tray top surface 610. In the kit-type tray 600 of FIG. 6., surgical instrument are stored inside the hollowed portion defined by the tray main body portion 640 and the tray top surface 610. In various exemplary embodiments, this enclosure may define a box accessed by lifting, pivoting or removing the top surface 610. However, in various other embodiments, the tray main body portion 640 may include a drawer which can be opened to provide access to the surgical instruments contained inside. In such a configuration, RF inventorying is performed by projecting an RF field 630 downward toward the bottom surface of the tray's main body portion 640. This RF field 630 will energize the RFID transponder tags of any instruments located inside the tray 600 and the RF transceiver unit contained in the enclosure 620 will then read the signals emitted by the energized tags Both the surface-type, tray-type and hybrid-type surgical instrument trays are known in the art. Any of the these types of surgical instrument trays may be used with this invention, as the invention derives its novelty not from the particular type of design, but rather the integrated RFID transceiver unit and visual indicator which permits an operator to quickly and accurately determine the status of a surgical instrument tray.

Figure 7:
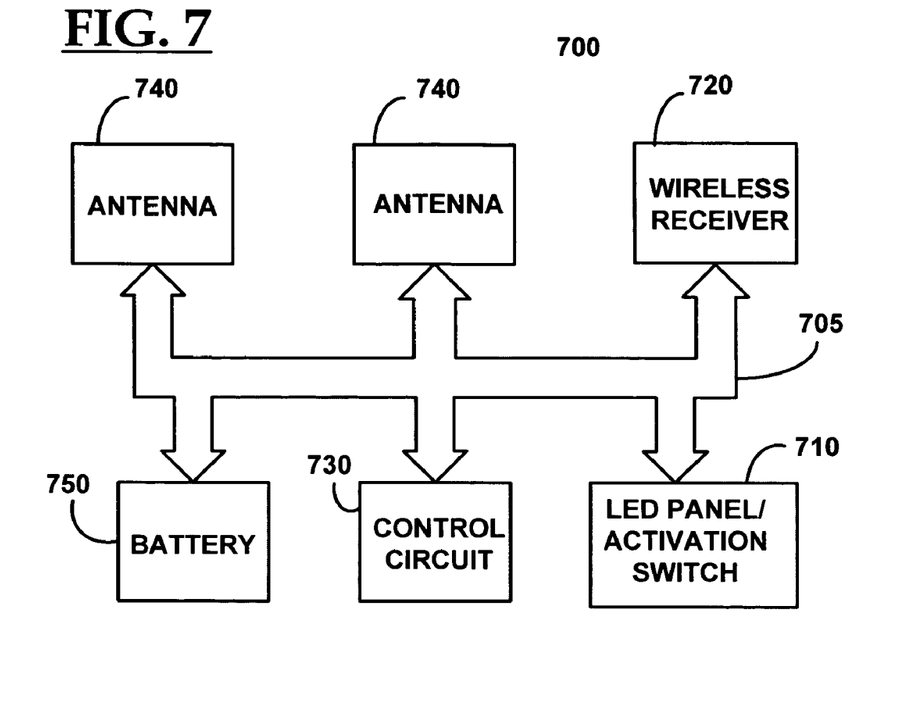
FIG. 7 is a block diagram illustrating various internal electrical components of an RFID enabled smart surgical instrument tray according to one embodiment of this invention.

Referring now to FIG. 7, a block diagram 700 is shown illustrating various internal electrical components of the RFID enabled smart surgical instrument tray according to one embodiment of this invention. As discussed above in the context of FIG. 4, these components include an LED panel including an activation switch 710, a wireless receiver 720 providing alternative activation means, a control circuit 730, a plurality of antennae 740 (in this example 2 are shown), and a battery 750, all of which are interconnected by a bus 705. The control circuit 730 may be a multipurpose computer, specific-purpose computer, application specific integrated circuit (ASIC), micro-controller, digital signal processor, or other suitable or control circuit. The antennae 740 are preferably two-way antennae capable of generating an RF field signal, and of receiving signals from one or more RFID transponder tags activated by the RF field.

During operation, in response to either a depression of the activation switch 710 or external activation through the wireless receiver 720, the control circuit 730 sends a command to the antennae 740 over the bus 705 causing the antennae 740 to generate an RF field in or on the instrument tray for a predetermined period of time. The RF field will cause any passive or active RFID transponder tags located within the tray or on the surface of the tray to become energized and to emit a signal containing their stored information. In various exemplary embodiments, the control circuit 730 may also send a signal to the LED panel 710 to illuminate a LED indicating that a read operation is in progress. Though such an LED is not shown in any of the figures, a third LED of a different color, such as a yellow LED, could be utilized in the LED panel to indicate that a read function is in progress.

Each transponder tag will emit a unique signal that is picked up by one or more of the antennae 740. All signals received by the antennae 740 are then passed to the control circuit 730 over the bus 705. In a preferred embodiment, the control circuit stores each received signal in a temporary memory and then performs a comparison operation between the received signals and information previously stored in a non-temporary memory of the control circuit 730 representing the surgical instruments that should be present with the particular tray. A determination that any surgical instruments are missing and/or the detection of any superfluous instruments will cause the control circuit 730 to send a signal to the LED panel 710 indicating a fail status by illuminating the red LED. Otherwise, the control circuit 730 will send a signal to the LED panel 710 indicating that a pass status by illuminating the green LED.

In various exemplary embodiments, in addition to merely confirming the presence of surgical instruments on the tray, the control circuit 730 will also perform other data analysis based on the information received from the transponder tags of the surgical instruments. In various exemplary embodiments, the information received from the transponder tags may also be compared against other conditions such as, for example, the maximum permitted length of service for each instrument. In various exemplary embodiments, if an instrument is found to have exceeded its maximum permitted length of service, this will also cause the control circuit 730 to indicate a fail status. Otherwise, if all conditions are satisfied for a given surgical instrument tray, a pass status will be indicated.

In various exemplary embodiments, if a fail status is indicated, a memory in the control circuit 730 of the smart instrument tray will store information identifying the specific reason(s) that fail status was indicated. A wireless device may be used to interrogate the smart surgical instrument tray and to access this memory so that a technician can determine the reason(s) that fail status was indicated and remedy the problem. In various exemplary embodiments, this information could be accessible through the wireless receiver 720 if the wireless receiver 720 functions as a wireless transceiver. Alternatively, this information could be stored by the control circuit 730 in an RF transponder-type memory that can written to by the control circuit 730 and accessed wirelessly by a portable, hand-held or fixed RF transceiver.

Figure 8:
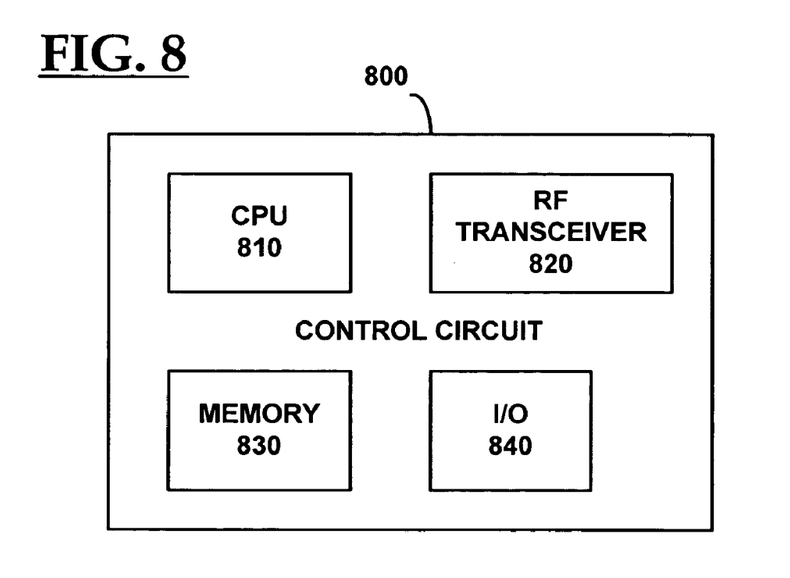
FIG. 8 is block diagram illustrating in greater detail, the internal components of an exemplary control circuit shown in FIG. 7 in accordance with one embodiment of this invention.

Referring now to FIG. 8, a block diagram is illustrated that shows in greater detail, the internal components of an exemplary control circuit 800 shown in FIG. 7 in accordance with one embodiment of this invention. The control circuit 800 in FIG. 8 includes a CPU 810, an RF transceiver unit 820, a memory 830 and an I/O bus 840. The I/O unit 840 receives activation commands either from the activation switch or from an external wireless source. In various exemplary embodiments, the I/O unit 840 will also send out a failure report through a wireless transceiver in response to a received command requesting that such a report be sent. The memory unit 830 preferably includes a volatile and a non-volatile portion. The volatile portion is used to store information read from RFID transponder tags by the RF transceiver unit 820. This information may be overwritten every time a read function is performed. The non-volatile portion of the memory unit 830 is used to store information including identification information of surgical instruments that are associated with a given instrument tray. In various exemplary embodiments, this information should not be rewritten or erased during subsequent read operations. However, it may be desirable, at various times after the initial programming, to reprogram or update this memory. In various exemplary embodiments, this reprogramming or updating is performed by an external wireless device through the wireless receiver and I/O unit 840.

Still referring to FIG. 8, the RF transceiver unit 820, in response to a command from the CPU 810 will cause the RF antennae to generate an RF field. Any RF transponder tags within the field will become energized by the field and will emit a signal including their stored information. The antennae will receive this signal and return it to the RF transceiver unit 820. In various exemplary embodiments, the RF transceiver until 820 may also update information stored in the RFID transponder tags of the surgical instruments if the tags are capable of memory updating.

Figure 9:
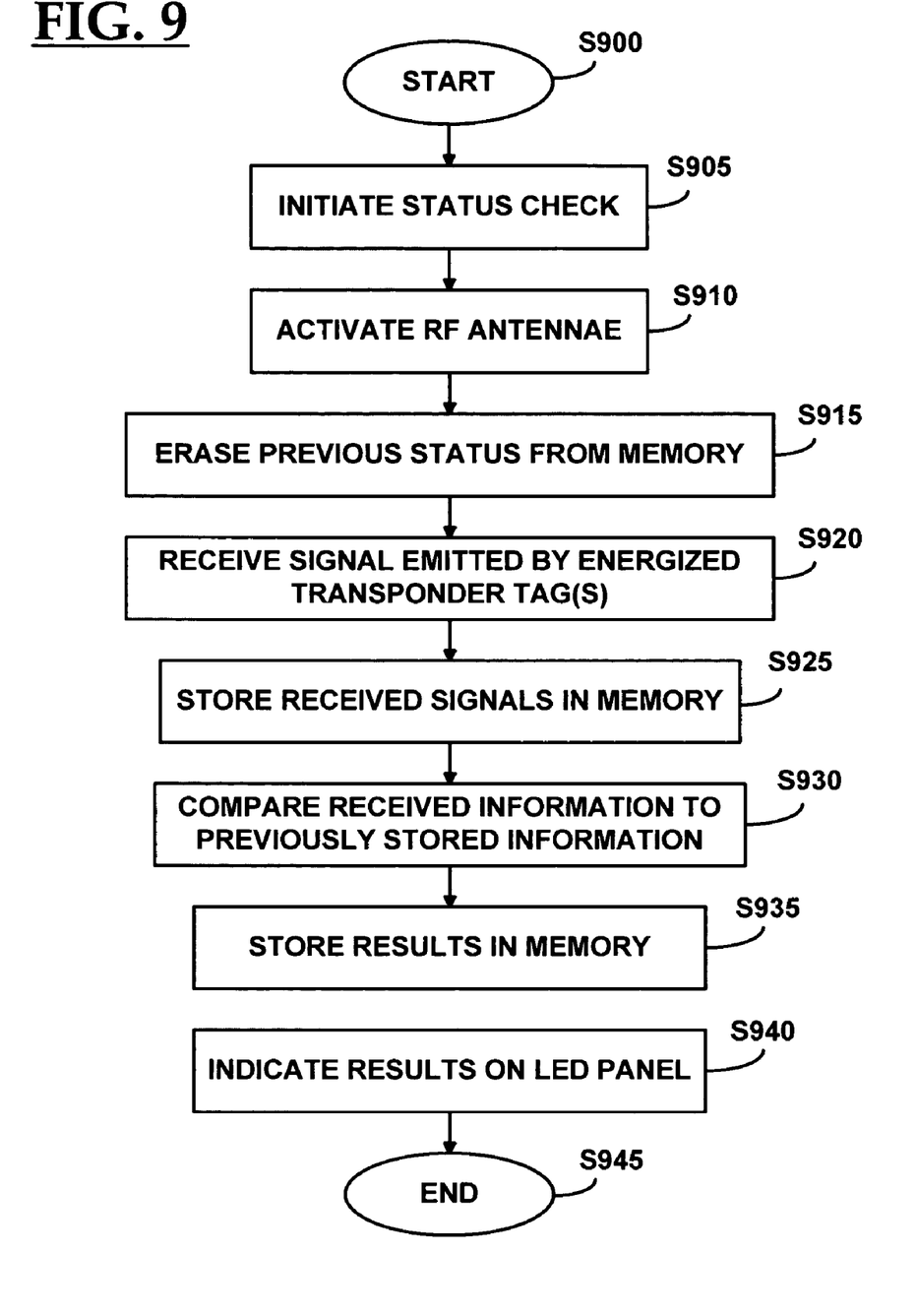
FIG. 9 is a flow chart illustrating the steps of a method of performing an inventory check with an RFID enabled smart surgical instrument tray according to one embodiment of this invention.

FIG. 9 is a flow chart illustrating the various procedures carried out in a method for reading RF transponder tags from surgical instruments and with a smart surgical instrument tray RF reader in accordance with various exemplary embodiments of this invention. Operation of the method begins in step S900 and proceeds to step S905 a status check is initiated. As discussed above, the status check may be initiated by depressing an activation switch or button or, alternatively, a status check may be initiated wirelessly from an external source. Next, operation of the method proceeds to step S910 where one or more RF antennae integral to the smart surgical instrument tray generate an RF field which is projected towards surface of the surgical instrument tray holding one or more surgical instruments. Then, in step S915, any information from a previous status check is erased from temporary memory. While the antennae remain activated for a sufficient period of time, operation of the method proceeds to step S920 where signals emitted by the energized transponder tags are received, and then, in step S925, stored in temporary memory.

After the time for activating the RF antennae has expired, operation of the method proceeds to step S930. In step S930, the identification information received from the RF transponder tags is compared against previously stored information identifying surgical instruments that should be associated with that tray. In addition, any other data analysis may be performed in this step on the received information. Next, in step S935, the results of the data analysis are stored in memory, and then, in step S940, an indication of the state of the surgical instrument tray is given by the LED status panel. As previously discussed, in a preferred embodiment, this indication will comprise illumination of either a green or red LED. For example, if in step S930 it is determined that the status is pass the pass LED is activated. Otherwise, if it is determined at step S930 that the status is fail the fail LED is activated. Optionally, the comparison and/or other data analysis in step S930 causes the fail LED to be activated, a report is generated indicating the specific reason for failure. This report is stored in memory in step S935 for later retrieval. Operation of the method terminates in step S945.

Through the foregoing embodiments, a smart surgical instrument tray reader apparatus is provided which will increase the accuracy and efficiency by which surgical instruments on the tray may be inventoried and monitored for usage. Furthermore, a rapid determination may be made if a given surgical instrument tray is complete or if any unrelated surgical instruments are present on the tray. Finally, other tracking functions may be facilitated such as time of usage.

While the foregoing description includes many details and specificities, it is to be understood that these have been included for purposes of explanation only, and are not to be interpreted as limitations of the present invention. Many modifications to the embodiments described above can be made without departing from the spirit and scope of the invention.

What is claimed:

1. An apparatus for identifying surgical instruments comprising:
   a surgical instrument tray for accommodating one or more surgical instruments;
   an RF transceiver unit, including a controller and one or more RF antenna transceivers, for projecting an RF field onto at least one surface of the surgical instrument tray to activate an RFID transponder tag associated with a surgical instrument and to receive a signal emitted by the RFID transponder tag, said RF transceiver unit integral to said surgical instrument tray;
   an activation switch located on at least one surface of the surgical instrument tray;
   a data processor electrically coupled to the RF transceiver unit, operable to compare the signal emitted by the RFID transponder tag with a value stored in memory;
   a visual indicator located at least one surface of the surgical instrument tray operable to give a visual indication of a current state of the surgical instrument tray based on the comparison; and
   a power supply electrically connected to said RF transceiver unit, said activation switch, said data processor, and said visual indicator.

2. The apparatus according to claim 1, wherein the activation switch is selected from the group consisting of a physical switch and a wireless receiver operable to receive an external activation command.

3. The apparatus according to claim 1, wherein the emitted signal comprises identification information for the surgical instrument to which the transponder tag corresponds.

4. The apparatus according to claim 1, wherein the value stored in memory comprises identification information for one or more surgical instruments that should be associated with that tray.

5. The apparatus according to claim 1, wherein the visual indicator comprises an LED panel with at least two different LED's, each LED operable to indicate a different result of said comparison.

6. The apparatus according to claim 1, wherein the data processor is further operable to generate a report stored in memory indicative of the results of said comparison.

7. The apparatus according to claim 1, wherein the power supply comprises a battery.

8. A method of performing an inventory function with an RF enabled surgical instrument tray comprising:
   activating the RF enabled surgical instrument tray;
   projecting an RF field at one or more surgical instruments of said instrument tray to active an RFID tag associated with each of the one or more surgical instruments;
   receiving a signal containing identification information from each RFID tag;
   comparing said identification information against previously stored data; and
   providing a visual indication of the results of said comparison.

9. The method according to claim 8, wherein the identification information comprises information selected from the group consisting of an identification name, an identification number, a manufacture name, a manufacture date, a date of first use, and a date of last update.

10. The method according to claim 9, the step of comparing further comprising comparing the identification information against stored identification information of surgical instruments that should correspond with the surgical instrument tray.

11. The method according to claim 10, the step of providing a visual indication further comprising illuminating a green LED if said received information matches said stored information and illuminating a red LED if said received information does not match said stored information.

12. A computer readable storage medium storing instructions therein for causing a computer processor to perform functions related to inventorying surgical instruments for use in an RFID enabled surgical instrument tray, the storage medium comprising:
   instructions for generating an RF field with one or more RF antenna transceivers to activate an RF transponder tag associated with each of one or more surgical instruments;
   instructions for receiving a signal emitted by each of the RF transponder tags containing identification information relating to items that the tags correspond to;
   instructions for comparing said identification information to information stored in a memory of said surgical instrument tray to determine if said identification information matches said stored information; and
   instructions for generating a visual indication of whether the identification information matches the stored information.

13. The computer readable storage medium according to claim 12, the identification information comprising information selected from the group consisting of an identification name, an identification number, a manufacture name, a manufacture date, a date of first use, and a date of last update.

14. The computer readable storage medium according to claim 12, the instructions for comparing said identification information to information stored in a database comprising instructions for comparing identification information of items on the surgical instrument tray with identification information of items that are known to correspond with that surgical instrument tray.

15. The computer readable storage medium according to claim 12, the instructions for generating a visual indication of whether said identification information matches said stored information further comprising instructions for illuminating one of a green LED and a red LED.

16. The computer readable storage medium according to claim 12, further comprising instructions for generating a report to be stored in memory when the identification information does not match the stored information.

17. The computer readable storage medium according to claim 12, further comprising instructions for writing new information to each of the transponder tags, the information including a date of current processing.

* * * * *